United States Patent [19]

Schlossman

[11] Patent Number: 5,314,683

[45] Date of Patent: May 24, 1994

[54] METHOD OF COUPLING COSMETIC MATERIALS AND COSMETICS CONTAINING COUPLED MATERIALS

[76] Inventor: David S. Schlossman, 250 Gorge Rd., Cliffside Park, N.J. 07010

[21] Appl. No.: 523,315

[22] Filed: May 14, 1990

[51] Int. Cl.$^5$ ............................................. A61K 7/021
[52] U.S. Cl. ........................................ 424/6.3; 424/64; 424/401
[58] Field of Search ................. 424/63, 64, 401; 524/423, 584, 586; 106/425

[56] References Cited

U.S. PATENT DOCUMENTS

| | | | |
|---|---|---|---|
| 3,196,079 | 7/1965 | Blaustein | 524/586 |
| 4,098,758 | 7/1978 | Monte et al. | 524/584 |
| 4,756,906 | 7/1988 | Sweeney | 424/63 |
| 4,801,445 | 1/1989 | Fukui | 514/844 |
| 4,877,604 | 10/1989 | Schlossman | 424/63 |
| 4,879,175 | 11/1989 | Urgo | 424/63 |
| 4,952,617 | 8/1990 | Ayala et al. | 106/419 |

*Primary Examiner*—Thurman K. Page
*Assistant Examiner*—D. Colucci
*Attorney, Agent, or Firm*—Handal & Morofsky

[57] ABSTRACT

A method of coupling organic and inorganic cosmetic materials is disclosed. Spherical shaped powders have beneficial characteristics as applied to cosmetics. These characteristics include uniform reflectivity, improved dispersion and superior viscosity characteristics in the final product. Coupling inorganic pigments to organic microspheres provides the benefits associated with the microspheres and allows a greater loading of inorganics into a cosmetic without sacrificing the benefits of the microspheres.

2 Claims, 8 Drawing Sheets

METHOD OF COUPLING COSMETIC MATERIALS AND COSMETICS CONTAINING COUPLED MATERIALS

TECHNICAL FIELD

The present invention relates to improved cosmetic products and the preparation of the same through coupling of cosmetic components with a titanate coupling agent.

BACKGROUND

Since prehistoric times, when body paint was first being applied, separation of Pigments and other components in paints and dyes has led to inconsistent colors and non-uniform applications of make-up. Separation and settling is a well-known phenomenon in liquid systems that results in diminished shelf-life, non-uniform colors and ineffectual application of make-up. Separation can also take place in Powder mixtures with the less dense material tending to concentrate in the upper volume of the mixture.

SUMMARY OF THE INVENTION

In a liquid system, improved dispersion may be achieved through reduction of surface area of the material being dispersed, i.e., spherical particles disperse more uniformly than cubic or irregular shaped particles. Improved dispersion also allows higher levels of material to be loaded into the dispersion.

The invention relates to the coupling of particulate components of a make-up. An organic and an inorganic material are coupled to provide a combination that is a homogeneous, uniform mixture that resists separation and disperses better than an uncoupled mixture of the same materials.

The inventive use of microspherical powders provides many useful characteristics for cosmetics including: a low surface area to volume ratio; improved dispersion; improved viscosity and better flow; and uniform reflectivity. commercially available microspherical powders include: polyethylene, polymethyl methacrylate, nylon, ethylene acrylates copolymer, polyvinylidene copolymer, silica, magnesium carbonate, and titanium dioxide. These microspherical powders are of diameters of 100 microns and less.

By coupling irregularly shaped or multi-faceted materials to the microspheres, the desirable characteristics of the microspherical powders may be imparted to these other materials. Essentially, microspheres of one of the materials are coated with the other material and the basic spherical shape is maintained. Alterations of the microspheres' characteristics may also be made to yield advantages in the resulting composition or processing of the composition.

The irregularly shaped materials should be ground or pulverized to a size smaller than the microspheres to enable the material to coat the microspheres without losing the spherical shape.

It has been discovered that a titanate coupling agent can join an organic material to an organic microspherical powder and join organic material to an inorganic microspherical powder. In joining the materials, moisture and air voids on the irregularly shaped material can be eliminated when these materials are coupled to the microsphere, thus tremendously reducing the surface area.

Liquid monalkoxy ($C_1$ to $C_{20}$) isostearoyl titanates, especially isopropyl triisostearoyl titanate, have been found effective as coupling agents in accordance with the invention.

A monohydrolyzable group attaches to a proton on the inorganic surface followed by hydrolysis or solvolysis, and then transesterification and transalkylation, whereupon the water of hydration and air voids are replaced by a monomolecular layer of organofunctional titanium and the titanate forms covalent bond (electron sharing) with a proton on the inorganic surface. The titanium is bonded to oxygen atoms and to the inorganic surface. The coated inorganic material is then able to be joined to an organic surface by the coating.

When coupling an organic polymer to pigment or extender pigment, the organic polymer may comprise as little as 15 percent by weight or less of the mixture and the titanate is present in amounts up to 5 percent by weight. Preferred compositions use the organic polymer microspheres in the amount of 15 to 35 percent by weight and isopropyl triisostearoyl titanate in amounts of 1 to 3 percent by weight.

Specific advantages of the coupled mixture include: improved hydrophobicity; a higher melting point; more uniform specific gravity and bulk density; improved dispersability; lower viscosities at comparable use levels; higher solids loading is possible; improved adhesion; smoother texture; unique surface area characteristics and reduced processing times and clean up is necessary.

When coupled, microspherical powders and fillers are useful in emulsions and poured powders. The advantages include: uniform specific gravity; a controlled oil absorption rate; lower specific surface area is achieved; maximum solid content for a given viscosity is achieved; minimum viscosity for a desired solids load is achieved; improved flowability and ease of dispersion; improved spreadibility and application; a unique surface texture (smooth/creamy) is achieved; and spherical particulate characteristics are maintained during processing. Organic polymer microspheric materials can thus be used to better incorporate pigments and fillers, or extender pigments, into a cosmetic.

These materials also yield advantages when incorporated into pressed powders. The powders are easier to press; the oil absorption rate is better controlled; packing is reduced; adhesion is improved; density is uniform; a smooth surface is achieved; and there is a reduced clean-up time in making and using the product.

The polymer microspheres used in cosmetics such as polyethylene may begin to soften at 95° C. to 110° C. and then deform or melt and flow. It is not unusual for these temperatures to be realized and exceeded in the processing of cosmetics.

By treating polymer microspheres mixed with an inorganic material such as boron nitride with a titanium coupling agent, insulated microspheres are achieved. The coating acts as insulation preventing the melting or deforming of the microspheres during processing. Thus, the dispersion advantages etc., due to microspherical shape are available in the final cosmetic product.

BEST MODE FOR CARRYING OUT THE INVENTION

In accordance with the inventive method of making an improved cosmetic component, one selects an organic microspherical material for cosmetic use. A pulverized inorganic material to be coupled to and carried by the organic microspherical marerial is combined with the microspherical material and the inorganic material to form a mixture. The liquid titanate coupling agent is added to the mixture and the resulting mixture is thoroughly mixed to form a mixture of microspherical compounds of inorganic material coupled to organic microspheres by the titanate coupling agent. Tests on specific coupled combinations have been performed and scanning electron microscope images have been made for components, mixtures and coupled mixtures.

Polyvinylidene copolymer (PVDC) microspheres have been combined with talc, with black iron oxide and with silica. Isopropyl triisostearoyl titanate was used as a coupling agent. Polyethylene was coupled with boron nitride using isopropyl triisostearoyl titanate. The amount of isopropyl triisostearoyl titanate was 2 percent by weight in all cases.

Talc was mixed with PVDC in a 15 to 85 ratio. The specific surface area of the mixture was 5.2 meters$^2$/gram, talc alone has a specific surface area of 8.0 meters$^2$/gram. When the mixture was treated, the specific surface area was reduced to 0.57 meters$^2$/gram.

A 20 percent composition of the treated talc-PVDC mixture in mineral oil was pourable with a measurable viscosity while a like composition using an untreated mixture formed a paste and had no flow property.

It was found that one gram of the treated material would float on 50 ml of water for more than an hour. This was not the situation without treatment. The treated mixture thus exhibits greatly increased hydrophobicity.

When PVDC and silicon were combined in a 15 to 85 ratio and treated with isopropyl triisostearoyl titanate, a float time for one gram of material on the surface of water was also in excess of one hour. When an untreated mixture was floated on water, the silica swiftly separated out and sank.

Polyethylene microspheres having a melt range of 105° to 106° C. was combined in a 50 to 50 ratio with boron nitride powder and treated with isopropyl triisostearoyl titanate. Again, the titanate amount was two percent by weight of the mixture. The melt range for the treated microspherical mixture was increased to more than 140° C.

The following scanning electron microscope photographs depict various microspheres, microsphere-irregular particulate mixtures and microspheres coupled with irregular particulates by isopropyl triisostearoyl titanate.

Figure 2:
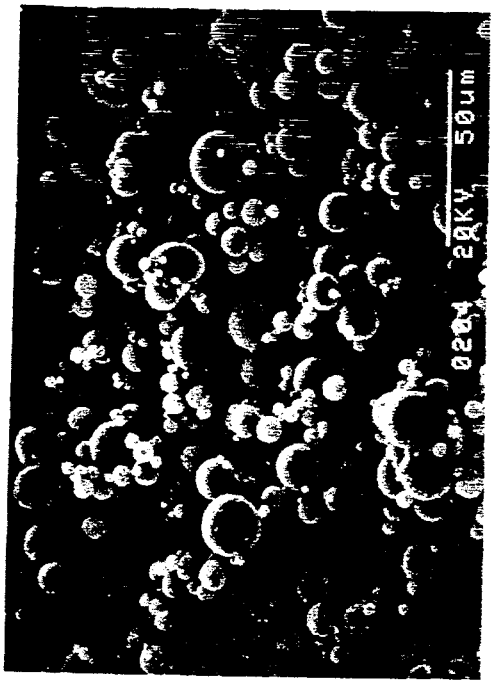
FIG. 2 depicts spherical polyethylene particles at a magnification of 600.
Figure 4:
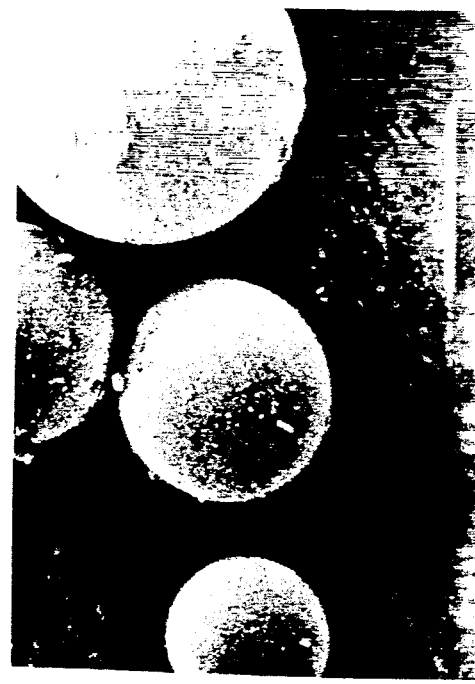
FIG. 4 depicts microspherical silica particles at a magnification of 2000.
Figure 1:
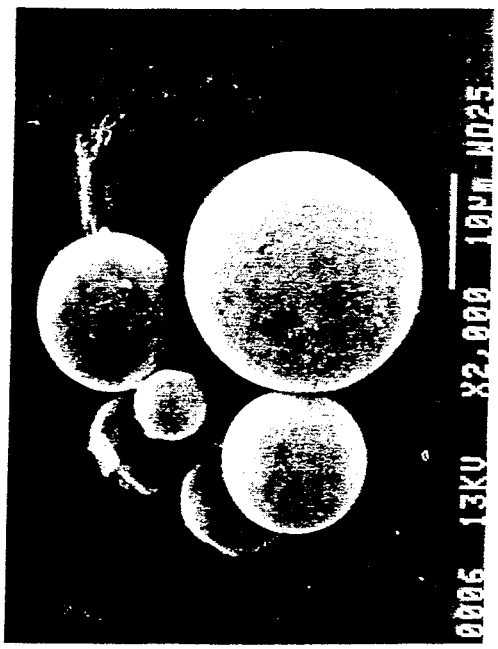
FIG. 1 depicts spherical polyvinylidene copolymer particles at a magnification of 2000.
Figure 3:
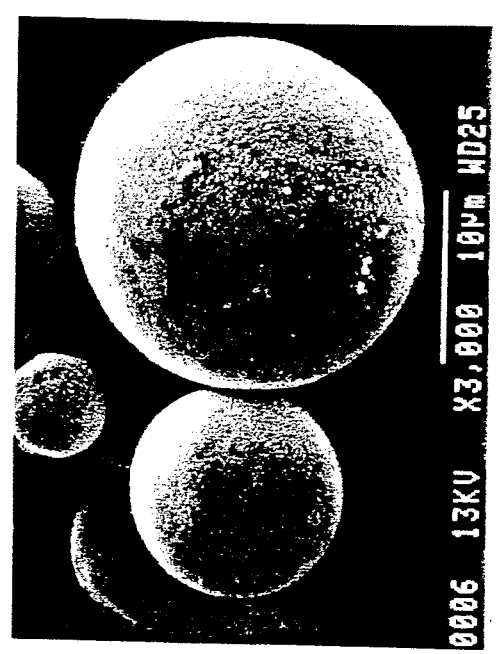
FIG. 3 depicts spherical polyvinylidene copolymer particles at a magnification of 3000.
Figure 6:
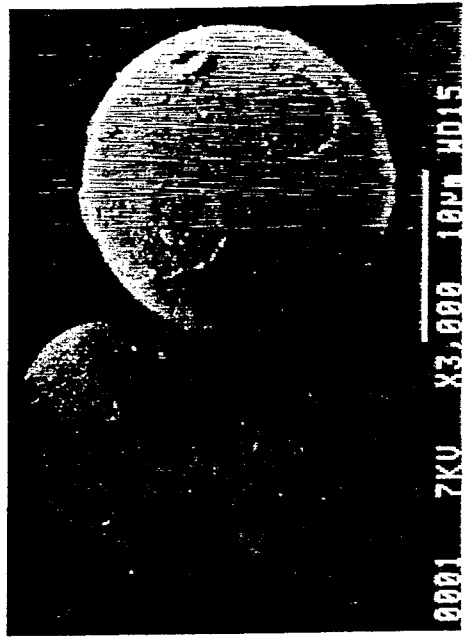
FIG. 6 depicts microspherical silica powder at a magnification of 3000.
Figure 8:
FIG. 8 depicts micronized talc particles at a magnification of 3000.
Figure 5:
FIG. 5 depicts boron nitride powder at a magnification of 3000.
Figure 7:
FIG. 7 depicts boron nitride powder at a magnification of 5000.
Figure 11:
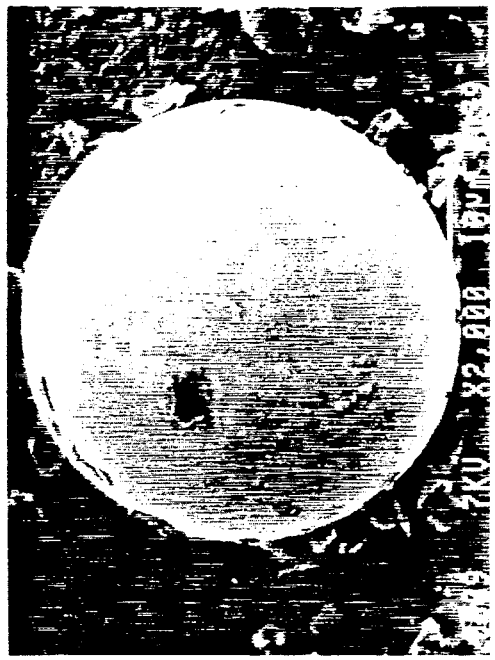
FIG. 11 depicts a mixture of spherical polyvinylidene copolymer and talc particles at a magnification of 2000.
Figure 9:
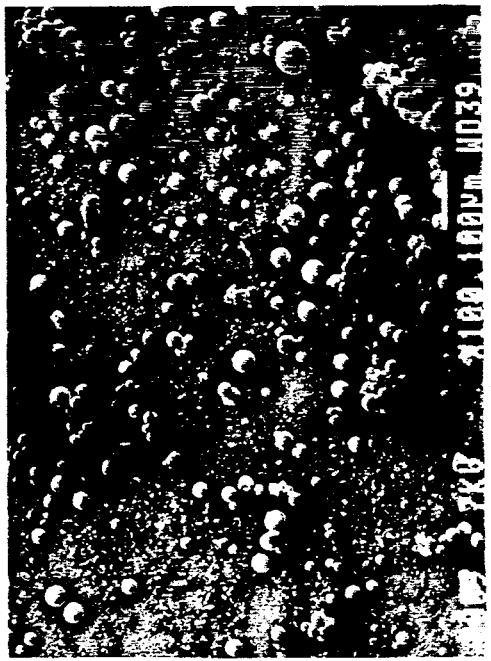
FIG. 9 depicts a mixture of spherical polyvinylidene copolymer and talc particles at a magnification of 100.
Figure 10:
FIG. 10 depicts a mixture of spherical polyvinylidene copolymer and talc particles at a magnification of 1000.
Figure 18:
FIG. 18 depicts spherical polyvinylidence copolymer particles coupled to black iron oxide particles by isopropyltriisostearoyl titanate, at a magnification of 2300.
Figure 16:
FIG. 16 depicts spherical polyvinylidene copolymer particles coupled to black iron oxide particles by isopropyltriisostearoyl titanate, at a magnification of 100.
Figure 17:
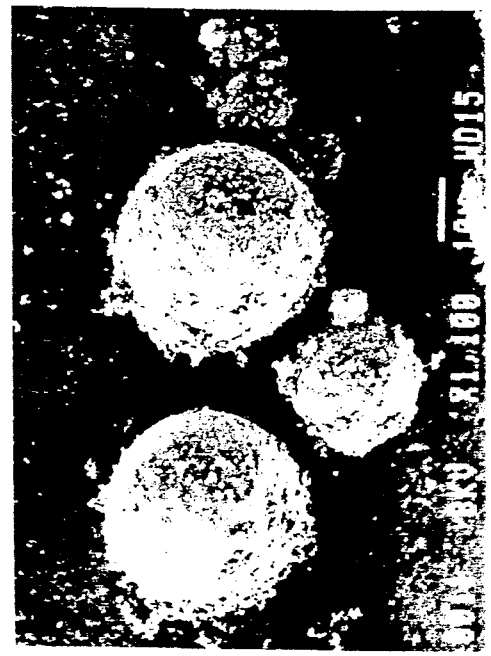
FIG. 17 depicts spherical polyvinylidene copolymer particles coupled to black iron oxide particles by isopropyltriisostearoyl titanate, at a magnification of 1100.
Figure 13:
FIG. 13 depicts spherical polyvinylidene copolymer particles coupled to talc particles by isopropyltriisostearoyl titanate, at a magnification of 1300.
Figure 15:
FIG. 15 depicts spherical polyvinylidene copolymer particles coupled to talc particles by isopropyltriisostearoyl titanate, at a magnification of 3000.
Figure 12:
FIG. 12 depicts spherical polyvinylidence copolymer particles coupled to talc particles by isopropyltriisostearoyl titanate, at a magnification of 100.
Figure 14:
FIG. 14 depicts spherical polyvinylidene copolymer particles coupled to talc particles by isopropyltriisostearoyl titanate, at a magnification of 2300.
Figure 21:
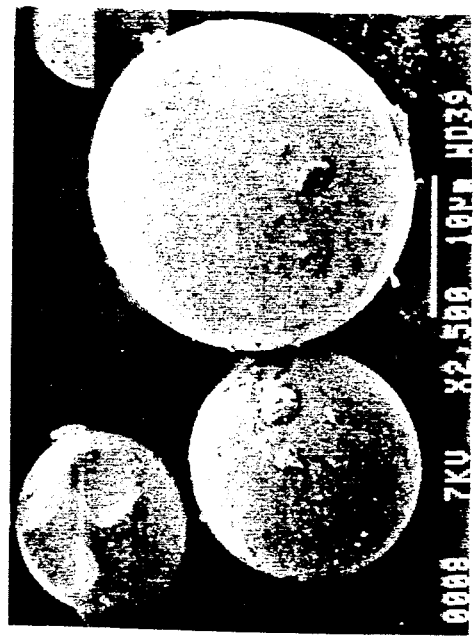
FIG. 21 depicts spherical polyvinylidence copolymer particles coupled to spherical silica particles by isopropyltriisostearoyl titanate, at a magnification of 2500.
Figure 19:
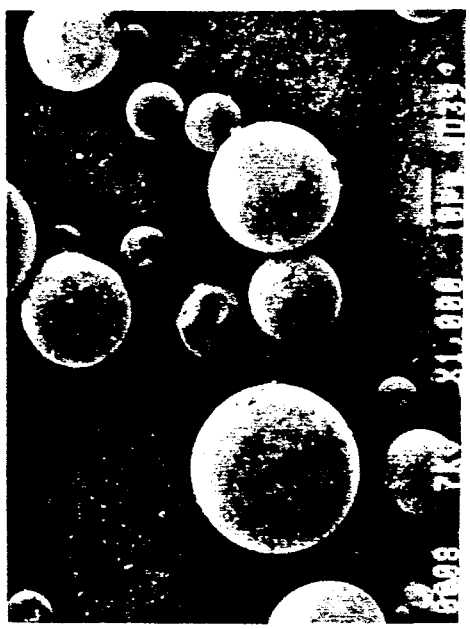
FIG. 19 depicts spherical polyvinylidene copolymer particles coupled to spherical silica particles by isopropyltriisostearoyl titanate, at a magnification of 1000.
Figure 20:
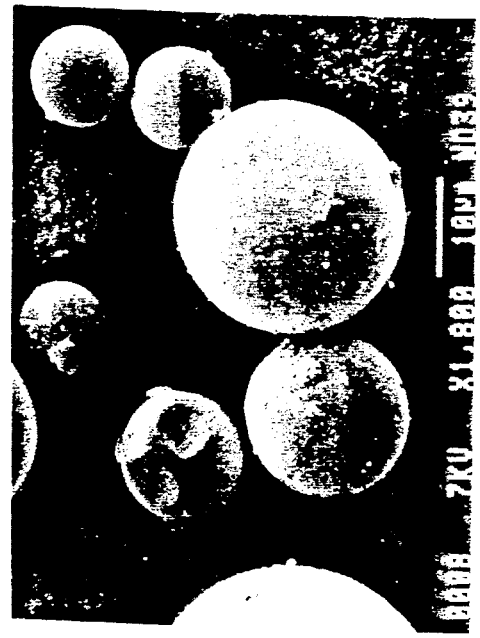
FIG. 20 depicts spherical polyvinylidence copolymer particles coupled to spherical silica particles by isopropyltriisostearoyl titanate, at a magnification of 1800.
Figure 24:
FIG. 24 depicts spherical polyethylene particles coupled to boron nitride particles by isopropyltriisostearoyl titanate, at a magnification of 3000.
Figure 22:
FIG. 22 depicts spherical polyethylene particles coupled to boron nitride particles by isopropyltriisostearoyl titanate, at a magnification of 300.
Figure 23:
FIG. 23 depicts spherical polyethylene particles coupled to boron nitride particles by isopropyltriisostearoyl titanate, at magnification of 1300.
Figure 27:
FIG. 27 depicts spherical polyethylene particles coupled to boron nitride particles by isopropyltriisostearoyl titanate, at a magnification of 4000.
Figure 25:
FIG. 25 depicts spherical polyethylene particles coupled to boron nitride particles by isopropyltriisostearoyl titanate, at a magnification of 450.
Figure 26:
FIG. 26 depicts spherical polyethylene particles coupled to boron nitride particles by isopropyltriisostearoyl titanate, at a magnification of 2000.

Photographs 1 to 8 show the shape of particular materials to be coupled and photographs 9, 10 and 11 depict the nonhomogeneity and uneven distribution of materials in a non-coupled mixture. Such inhomogeneity leads to uneven dispersion, accelerated separation and other problems. Photographs 12 to 27 show the coupled mixtures and the spherical nature of the microspheres remaining intact after being coated with the irregularly shaped material.

The inorganic materials are much denser than the organic polymers and therefore significant loading in terms of weight of the inorganic material is achievable while maintaining the spherical shape of the coupled materials.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. An improved hydrophobic, low bulk density dispersible, high-loading cosmetic material with a low surface area-to-volume ratio, comprising a pulverized inorganic cosmetic pigment material coating coupled to from 15 to 35% of an organic polymeric microspherical powder of diameter less than 100 microns said microspherical powder being selected from the group consisting of polyethylene, polymethylmethacrylate and nylon copolymers by from 1 to 5% of a titanate coupling agent said coupling agent wherein the inorganic material has a particle size sufficiently smaller than the organic microspheres that the coupled product has a generally spherical particulate shape, said inorganic cosmetic material and said cosmetic material being capable of being coupled by said titanate coupling agent.

2. A cosmetic material according to claim 1 wherein said titanate coupling agent is a liquid monalkoxy ($C_1$ to $C_{20}$) isostearoyl titanate.

* * * * *